United States Patent
Rader et al.

(10) Patent No.: US 6,231,937 B1
(45) Date of Patent: May 15, 2001

(54) ANIMAL AND RODENT REPELLING GARBAGE BAG

(76) Inventors: Karen Rader, 610 W. Pierson, Hamilton, TX (US) 76531; Connie Jones, P.O. Box 697, Proctor, TX (US) 76468

(*) Notice: Subject to any disclaimer, the term of this patent is extended or adjusted under 35 U.S.C. 154(b) by 0 days.

(21) Appl. No.: 09/226,264

(22) Filed: Jan. 7, 1999

(51) Int. Cl.$^7$ .............................. A01N 25/34; B05D 1/02
(52) U.S. Cl. .................. 428/35.2; 428/35.5; 428/35.7; 428/34.3; 424/411; 424/412; 424/414; 427/421
(58) Field of Search ................. 428/34.3, 35.2, 428/35.5, 35.7, 521, 523; 424/409, 411, 412, 414, 416; 427/421

(56) References Cited

U.S. PATENT DOCUMENTS

| | | | | |
|---|---|---|---|---|
| 4,169,898 | * | 10/1979 | Haase | 424/331 |
| 4,555,015 | * | 11/1985 | Haase | 206/0.5 |
| 4,870,100 | * | 9/1989 | Wolf | 514/461 |
| 5,013,551 | * | 5/1991 | Atkinson | 424/412 |
| 5,674,496 | * | 10/1997 | Etscorn et al. | 424/195.1 |

* cited by examiner

Primary Examiner—Rena L. Dye

(57) ABSTRACT

An animal repelling garbage bag composition is provided including a garbage bag and a mixture applied to the garbage bag for repelling animals therefrom.

15 Claims, 2 Drawing Sheets

ANIMAL AND RODENT REPELLING GARBAGE BAG

BACKGROUND OF THE INVENTION

1. Field of the Invention

The present invention relates to trash bags and more particularly pertains to a new animal and rodent repelling garbage bag for repelling animals from a garbage bag and the contents thereof.

2. Description of the Prior Art

The use of trash bags is known in the prior art. More specifically, trash bags heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,674,496; U.S. Pat. No. 3,132,992; U.S. Pat. No. 4,320,112; U.S. Pat. No. 4,944,393; U.S. Pat. No. 3,767,785; and U.S. Pat. Des. 330,852.

In these respects, the animal and rodent repelling garbage bag according to the present invention substantially departs from the conventional concepts and designs of the prior art, and in so doing provides an apparatus primarily developed for the purpose of repelling animals from a garbage bag and the contents thereof.

SUMMARY OF THE INVENTION

In view of the foregoing disadvantages inherent in the known types of trash bags now present in the prior art, the present invention provides a new animal and rodent repelling garbage bag construction wherein the same can be utilized for repelling animals from a garbage bag and the contents thereof.

The general purpose of the present invention, which will be described subsequently in greater detail, is to provide a new animal and rodent repelling garbage bag apparatus and method which has many of the advantages of the trash bags mentioned heretofore and many novel features that result in a new animal and rodent repelling garbage bag which is not anticipated, rendered obvious, suggested, or even implied by any of the prior art trash bags, either alone or in any combination thereof.

To attain this, the present invention generally comprises a garbage bag having an impermeable, flexible inelastic sheet. Such sheet is preferably constructed from a polyethylene material and includes a side wall. This side wall defines a closed bottom and an open top. Impregnated within the sheet of the garbage bag is a mixture for repelling animals therefrom. As shown in FIG. 1, the mixture preferably includes effective amounts of methlynonylketone, pine cleaner, boric acid, ammonia, cayenne pepper.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new animal and rodent repelling garbage bag apparatus and method which has many of the advantages of the trash bags mentioned heretofore and many novel features that result in a new animal and rodent repelling garbage bag which is not anticipated, rendered obvious, suggested, or even implied by any of the prior art trash bags, either alone or in any combination thereof.

It is another object of the present invention to provide a new animal and rodent repelling garbage bag which may be easily and efficiently manufactured and marketed.

It is a further object of the present invention to provide a new animal and rodent repelling garbage bag which is of a durable and reliable construction.

An even further object of the present invention is to provide a new animal and rodent repelling garbage bag which is susceptible of a low cost of manufacture with regard to both materials and labor, and which accordingly is then susceptible of low prices of sale to the consuming public, thereby making such animal and rodent repelling garbage bag economically available to the buying public.

Still yet another object of the present invention is to provide a new animal and rodent repelling garbage bag which provides in the apparatuses and methods of the prior art some of the advantages thereof, while simultaneously overcoming some of the disadvantages normally associated therewith.

Still another object of the present invention is to provide a new animal and rodent repelling garbage bag for repelling animals from a garbage bag and the contents thereof.

Even still another object of the present invention is to provide a new animal and rodent repelling garbage bag including a garbage bag and a mixture applied to the garbage bag for repelling animals therefrom.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
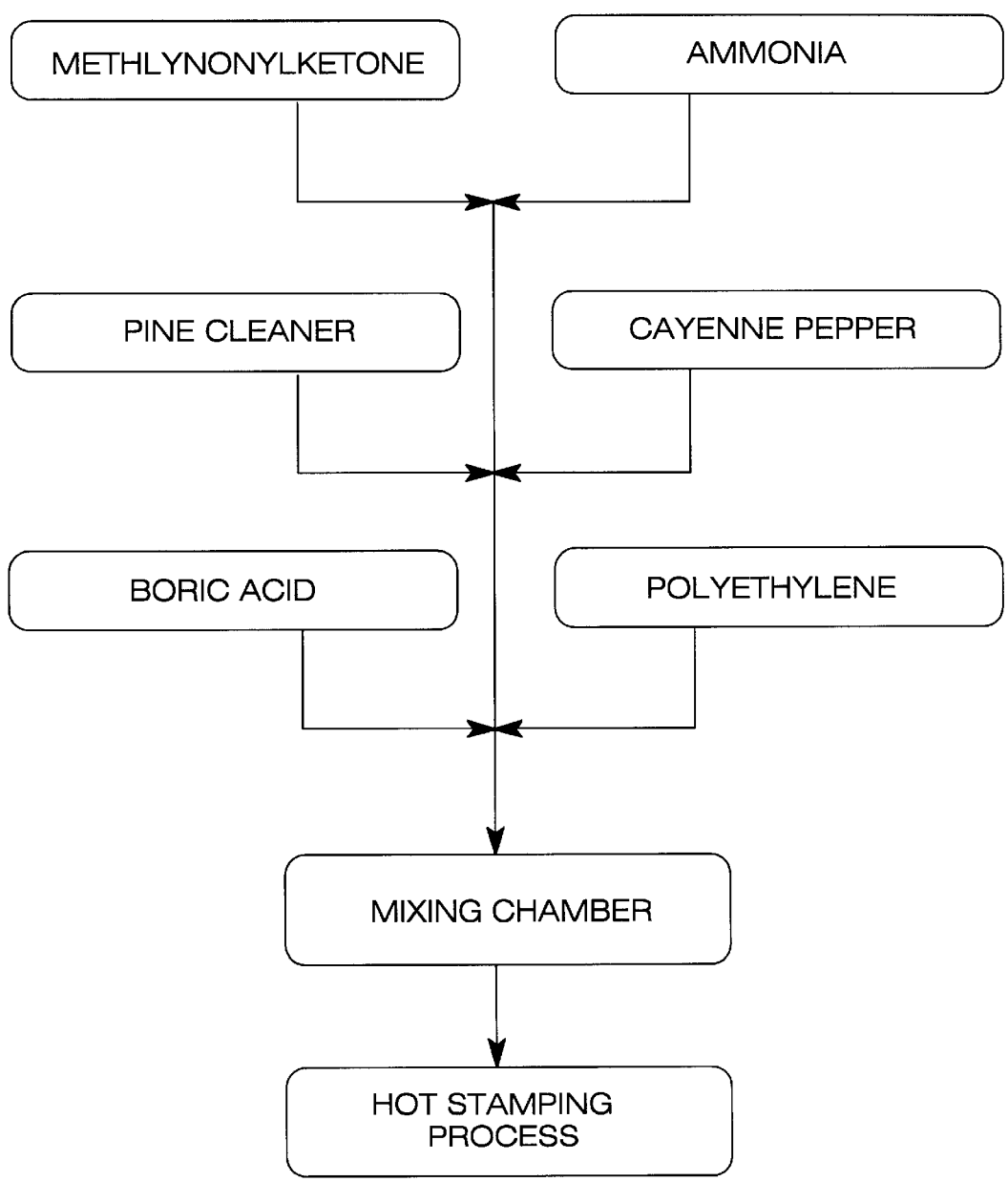
FIG. 1 is a flow chart delineating the various components of the present invention.
Figure 2:
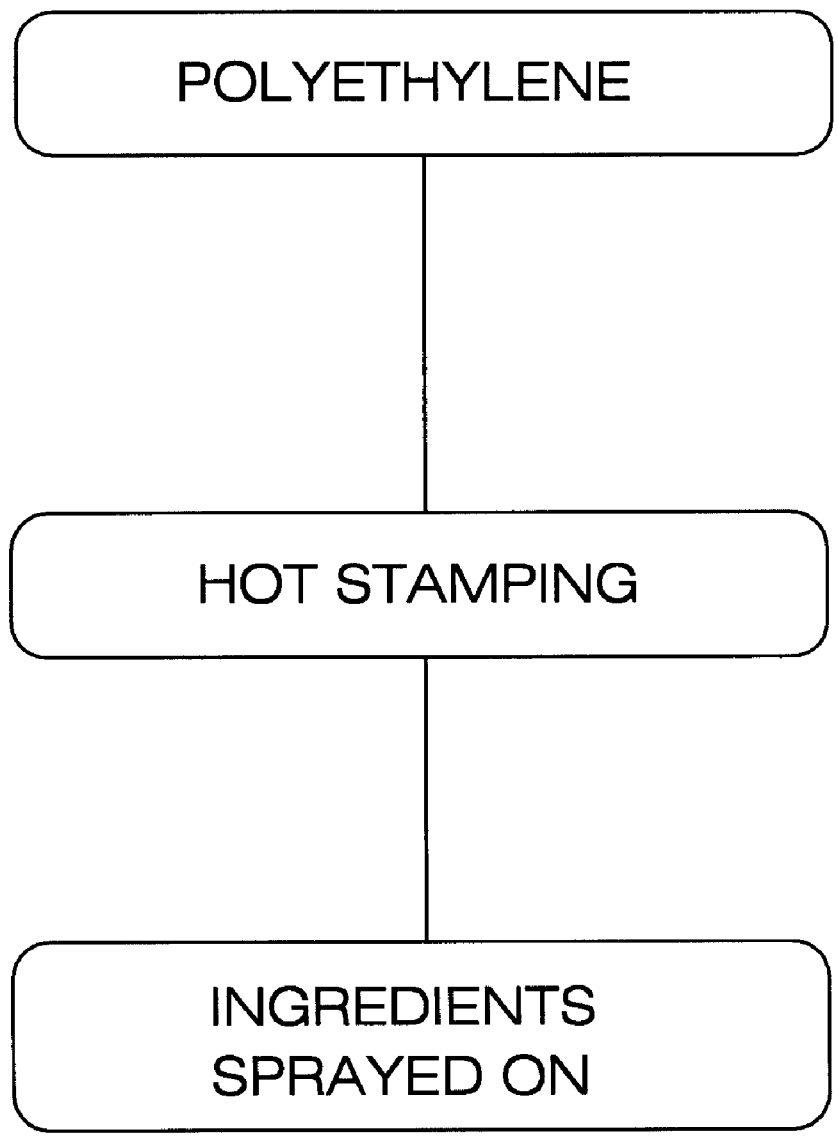
FIG. 2 is a flow chart delineating the various components of another embodiment of the present invention.

With reference now to the drawings, and in particular to FIGS. 1 & 2 thereof, a new animal and rodent repelling garbage bag embodying the principles and concepts of the present invention and generally designated by the reference numeral 10 will be described.

The present invention, designated as numeral 10, includes a garbage bag having an impermeable, flexible inelastic sheet. Such sheet is preferably constructed from a polyethylene material and includes a side wall. This side wall defines a closed bottom and an open top.

Impregnated within the sheet of the garbage bag is a mixture for repelling animals therefrom. As shown in FIG. 1, the mixture preferably includes effective amounts of methlynonylketone, pine cleaner, boric acid, ammonia, cayenne pepper. Impregnation may be accomplished by a plurality of modules being formed in the sheet of the garbage bag which each impregnated with the mixture. In the alternative, the mixture may simply combined with the polyethylene prior to use after which the composition is mixed in a chamber and stamped to form the thin sheet.

It should be noted any each of the foregoing components may be added in any random amount. Ideally, the amounts of methlynonylketone, pine cleaner, boric acid, ammonia, and cayenne pepper are sufficient to produce an odor of desired strength. The amounts of such ingredients may also vary depending on the amount of polyethylene employed in making the garbage bag.

An alternate method associated with the present invention will now be set forth. Such method first includes the steps of providing each of the components of the aforementioned mixture. Once provided, such mixture is placed in a spray bottle which may be used to spray a conventional garbage bag that is constructed using polyethylene. Note FIG. 2. With use of either the method or apparatus, the present invention eliminates the problem of garbage bags being torn by animals and the resulting mess. As an option, the garbage bag may take on any size and further have printed thereon kitchen accessories, ducks, geese, vegetables, etc.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An animal repelling garbage bag system comprising, in combination:

a garbage bag including an impermeable, flexible inelastic sheet constructed from a polyethylene material and including a side wall with a closed bottom and an open top;

a mixture impregnated within the sheet of the garbage bag for repelling animals therefrom;

said mixture including methlynonylketone;

said mixture including a pine oil based cleaner;

said mixture including boric acid;

said mixture including ammonia; and said mixture including cayenne pepper.

2. An animal repelling garbage bag composition comprising:

a garbage bag;

a mixture applied to the garbage bag for repelling animals therefrom;

wherein said mixture includes boric acid; and wherein said mixture includes a pine oil based cleaner.

3. An animal repelling garbage bag composition as set forth in claim 2 wherein said mixture includes methlynonylketone.

4. An animal repelling garbage bag composition as set forth in claim 2 wherein said mixture includes ammonia.

5. (Amended) An animal repelling garbage bag composition comprising:

a garbage bag;

a mixture applied to the garbage bag for repelling animals therefrom;

wherein said mixture includes boric acid; and wherein said mixture includes cayenne pepper.

6. An animal repelling garbage bag composition as set forth in claim 5 wherein said mixture includes a pine oil based cleaner.

7. An animal repelling garbage bag composition as set forth in claim 5 wherein said mixture includes methlynonylketone.

8. An animal repelling garbage bag composition as set forth in claim 5 wherein said mixture includes ammonia.

9. A method of repelling animals from a garbage bag, the method comprising the steps of:

providing a garbage bag;

providing a mixture for repelling animals therefrom;

spraying the mixture on the garbage bag;

wherein said mixture includes boric acid;

wherein said mixture includes a pine oil based cleaner.

10. A method as set forth in claim 9 wherein said mixture includes methlynonylketone.

11. A method as set forth in claim 9 wherein said mixture includes ammonia.

12. A method of repelling animals from a garbage bag, the method comprising the steps of:

providing a garbage bag;

providing a mixture for repelling animals therefrom;

spraying the mixture on the garbage bag;

wherein said mixture includes boric acid; and wherein said mixture includes cayenne pepper.

13. A method as set forth in claim 12 wherein said mixture includes a pine oil based cleaner.

14. A method as set forth in claim 12 wherein said mixture includes methlynonylketone.

15. A method as set forth in claim 12 wherein said mixture includes ammonia.

* * * * *